+ 
US008617869B2

(12) United States Patent
Culver et al.

(10) Patent No.: US 8,617,869 B2
(45) Date of Patent: Dec. 31, 2013

(54) METAL COATED VIRUS-BASED NANOELECTRODES AND METHOD OF ASSEMBLING OF SAME

(75) Inventors: James N. Culver, Potomac, MD (US); Michael Harris, Lafayette, IN (US); Elizabeth Royston, Columbia, MD (US)

(73) Assignees: University of Maryland, College Park, College Park, MD (US); Purdue Research Foundation, West Lafayette, IN (US)

( * ) Notice: Subject to any disclaimer, the term of this patent is extended or adjusted under 35 U.S.C. 154(b) by 1016 days.

(21) Appl. No.: 12/520,968

(22) PCT Filed: Dec. 28, 2007

(86) PCT No.: PCT/US2007/089032
§ 371 (c)(1),
(2), (4) Date: Dec. 22, 2009

(87) PCT Pub. No.: WO2008/147471
PCT Pub. Date: Dec. 4, 2008

(65) Prior Publication Data
US 2010/0093562 A1 Apr. 15, 2010

Related U.S. Application Data

(60) Provisional application No. 60/877,403, filed on Dec. 28, 2006.

(51) Int. Cl.
*C12N 7/00* (2006.01)
*C12N 7/01* (2006.01)
*H01M 4/00* (2006.01)
*H01M 4/02* (2006.01)
*H01M 4/04* (2006.01)
*B01J 23/75* (2006.01)
*B01J 23/755* (2006.01)

(52) U.S. Cl.
USPC ........ 435/235.1; 435/236; 977/802; 977/705; 429/209

(58) Field of Classification Search
USPC ......... 977/705, 802; 435/235.1, 236; 429/209
See application file for complete search history.

(56) References Cited

U.S. PATENT DOCUMENTS

2004/0028694 A1 2/2004 Young et al.
2004/0197884 A1 10/2004 Okuda et al.

FOREIGN PATENT DOCUMENTS

WO 2004065928 8/2004

OTHER PUBLICATIONS

Knez et al. (Adv. Funct. Mater., 2004, 14(2):116-124).*
Wang, P. Nanoscale biocatalyst systems. *Curr Opin Biotechnology* 2006, 17, 574-579.

(Continued)

*Primary Examiner* — Christopher M Babic
*Assistant Examiner* — Jeremy C Flinders
(74) *Attorney, Agent, or Firm* — Marianne Fuierer; Moore & Van Allen, PLLC

(57) ABSTRACT

The present invention relates to high content surface areas containing nickel and/or cobalt metallic compounds assembled on a modified Tobacco mosaic virus (TMV) template, wherein the modified TMV template is engineered to encode unique placement of cysteine residues that self-assemble onto gold patterned surfaces in a substantially aligned fashion, producing a >10 fold increase in surface area. Deposition of ionic metals onto the surface assembled virus templates produce uniform metal coatings for the fabrication of oriented high surface area materials.

16 Claims, 10 Drawing Sheets

(56) References Cited

OTHER PUBLICATIONS

Yang, S. M.; Jang, S. G.; Choi, D. G.; Kim, S.; Yu, H. K. Nanomachining by colloidal lithography. *Small* 2006, 2, (4), 458-475.

Braun, E.; Eichen, Y.; Sivan, U.; Ben-Yoseph, G. DNA-templated assembly and electrode attachment of a conducting silver wire. *Nature* 1998, 391, (6669), 775-778.

Flynn, C. E.; Lee, S. W.; Peelle, B. R.; Belcher, A. M. Viruses as vehicles for growth, organization and assembly of materials. *Acta Materialia* 2003, 51, (19), 5867-5880.

Mertig, M.; Kirsch, R.; Pompe, W. Biomolecular approach to nanotube fabrication. *Applied Physics A* 1998, 66, S723-S727.

Behrens, S.; Wu, J.; Habicht, W.; Unger, E. Silver nanoparticles and nanowire formation by microtubule templates. *Chemistry of Materials* 2004, 16, (16), 3085-3090.

Gao, X. Y.; Matsui, H. Peptide-based nanotubes and their application in bionanotechnology. *Advanced Materials* 2005, 17, (17), 2037-2050.

Matsui, H.; Pan, S.; Gologan, B.; Jonas, S. H. Bolaamphiphile nanotube-templated metallixed Wires. *Journal of Physical Chemistry B* 2000, 104, (41), 9576-9579.

Keren, K.; Berman, R. S.; Buchstab, E.; Sivan, U.; Braun, E. DNA-templated carbon nanotube field-effect transistor. *Science* 2003, 302, (5649), 1380-1382.

Nam, K. T.; Kim, D. W.; Yoo, P. J.; Chiang, C. Y.; Meethong, N.; Hammond, P. T.; Chiang, Y. M.; Belcher, A. M. Virus-enabled synthesis and assembly of nanowires for lithium ion battery electrodes. *Science* 2006, 312, (5775), 885-888.

Knez, M.; Bittner, A. M.; Boes, F.; Wege, C.; Jeske, H.; Maiss, E.; Kern, K. Biotemplate synthesis of 3-nm nickel and cobalt nanowires. *Nano Letters* 2003,3, (8), 1079-1082.

Dujardin, E.; Peet, C.; Stubbs, G.; Culver, J. N.; Mann, S. Organization of metallic nanoparticles using tobacco mosaic virus templates. *Nano Letters* 2003, 3, (3), 413-417.

Yoo, P. J.; Nam, K. T.; Qi, J.; Lee, S.-K.; Park, J.; Belcher, A. M.; Hammond, P. T. Spontaneous assembly of viruses on multilayered polymer surfaces. *Nat Mater* 7 2006, 5, (3), 234-240.

Tseng, R. J.; Tsai, C. L.; Ma, L. P.; Ouyang, J. Y. Digital memory device based on tobacco mosaic virus conjugated with nanoparticles. *Nature Nanotechnology* 2006, 1, (1), 72-77.

Knez, M.; Sumser, M.; Bittner, A. M.; Wege, C.; Jeske, H.; Kooi, S.; Burghard, M.; Kern, K. Electrochemical modification of individual nano-objects. *Journal of Electroanalytical Chemistry* 2002, 522, (1), 70-74.

Shenton, W.; Douglas, T.; Young, M.; Stubbs, G.; Mann, S. Inorganic-organic nanotube composites from template mineralization of tobacco mosaic virus. *Advanced Materials* 1999, 11, (3), 253-256.

Liu, W. L.; Alim, K.; Balandin, A. A.; Mathews, D. M.; Dodds, J. A. Assembly and characterization of hybrid virus inorganic nanotubes. *Applied Physics Letters* 2005, 86, (25), 1-3.

Balci, S.; Bittner, A. M.; Hahn, K.; Scheu, C.; Knez, M.; Kadri, A.; Wege, C.; Jeske, H.; Kern, K. Copper nanowires within the central channel of tobacco mosaic virus particles. *Electrochimica Acta* 2006, 51, (28), 6251-6257.

Lee, S. Y.; Royston, E.; Culver, J. N.; Harris, M. T. Improved metal cluster deposition on a genetically engineered tobacco mosaic virus template. *Nanotechnology* 2005, 16, (7), S435-S441.

Lee, S. W.; Mao, C. B.; Flynn, C. E.; Belcher, A. M. Ordering of Quantum Dots Using Gentically Engineered Viruses. *Science* 2002, 296, (5569), 892-895.

Schlick, T. L.; Ding, Z. B.; Kovacs, E. W.; Francis, M. B. Dual-surface modification of the tobacco mosaic virus. *Journal of the American Chemical Society* 2005, 127, (11), 3718-3723.

Royston, E.; Lee, S. Y.; Culver, J. N.; Harris, M. T. Characterization of silica-coated tobacco mosaic virus. *J Colloid Interface Sci* 2006, 298, (2), 706-712.

Namba, K.; Pattanayek, R.; Stubbs, G. Visualization of protein-nucleic acid interactions in a viru. *Journal of Molecular Biology* 1989, 208, (2), 307-325.

Knez, M.; Sumser, M.; Bittner, A. M.; Wege, C.; Jeske, H.; Martin, T. P.; Kern, K. Spatially selective nucleation of metal clusters on the tobacco mosaic virus. *Advanced Functional Materials* 2004, 14, (2), 116-124.

Stubbs, G. Molecular structures of viruses from the tobacco mosaic virus group. *Seminars in Virology* 1990, 1, 405-412.

Lee, S. Y.; Choi, J.; Royston, E.; Janes, D. B.; Culver, J. N.; Harris, M. T. J Nanosci. Deposition of platinum clusters on surface-modified tobacco mosaic virus. *Nanotechnol* 2006, 6, (4), 974-81.

Yi, H.; Nisar, S.; Lee, S. Y.; Powers, M. A.; Bentley, W. E.; Payne, G. F.; Ghodssi, R.; Rubloff, G. W.; Harris, M. T.; Culver, J. N. Patterned assembly of genetically modified viral nanotemplates via nucleic acid hybridization. *Nano Lett* 2005, 5, (10), 1931-6.

Carley, A. F.; Jackson, S. D.; O'Shea, J. N.; Roberts, M. W. The formation and characterization of Ni3+- an x-ray photoelectron spectroscopic investigation of potassium-doped Ni(110)-0. *Surface Science* 1999, 440, (3), L868-L874.

Siconolfi, D. J.; Frankenthal, R. P. Air oxidation of Ni-p. alloy. *Journal of the Electrochemical Society* 1989, 136, (9), 2475-2480.

Grosvenor, A. P.; Biesinger, M. C.; Smart, R. S.; McIntyre, N. S. New interpretation of XPS spectra of nickel metal and oxides. *Surface Science* 2006, 600, (9), 1771-1779.

Gooding, G. V.; Hebert, T. T. A simple technique for purification of tobacco mosaic virus. *Phytopathology* 1967, 57, (11), 1285.

Yi, H.; Rubloff, G. W.; Culver, J. N. The microarrays: Hybridization based assembly of DNA-programmed viral nanotemplates. *Langmuir* 2007, 23, (5), 2663-2667.

Royston, E.; Lee, S-Y; Culver, J.; Harris, M. Characterization of silica-coated tobacco mosaic virus. *Journal of Colloid and Interface Science* 298 (2006) 706-712.

Clark, W.G.; Fitchen, J.; Nejidat, A.; Deom, C.M; Beachy, R.N. Studies of coat protein-mediated resistance to tobacco mosaic virus (TMV). II. Challenge by a mutant with altered virion surgace does not overcome resistance conferred by TMV coat protein. *Journal of General Virology* (1995), 76, 2613-17.

Tsugita, A.; Gish, D.T.; Young, J.; Fraenkel-Conrat, H.; Knight, C.A.; Stanley, W.M. The Complete Amino Acid Sequence of the Protien of Tobacco Mosaic Virus. *Biochemistry*. vol. 46, 1960 pp. 1463-1469.

Creager, A.; Scholthof, K-B.; Citovsky, V.; Scholthof, H.B. Tobacco Mosaic Virus: Pioneering Research for a Century. Meeting Report, The Plant Cell. Mar. 1999, pp. 301-308.

Dawson, W.O.; Beck, D.L.; Knorr, D.A.; Grantham, G.L. cDNA cloning of the complete genome of tobacco mosaic virus and production of infections transcripts. *Proc. Natl. Acad. Sci. USA*, vol. 83, Mar. 1986, pp. 1832-1836.

Royston, E. et al. "Self-Assembly of Virus-Structured High Surface Area Nanomaterials and Their Application as Battery Electrodes", LANGMUIR, vol. 24, Dec. 23, 2007, pp. 906-912.

European Office Action, corresponding to European Patent Application No. 07 875 051.0, dated Nov. 7, 2012.

* cited by examiner

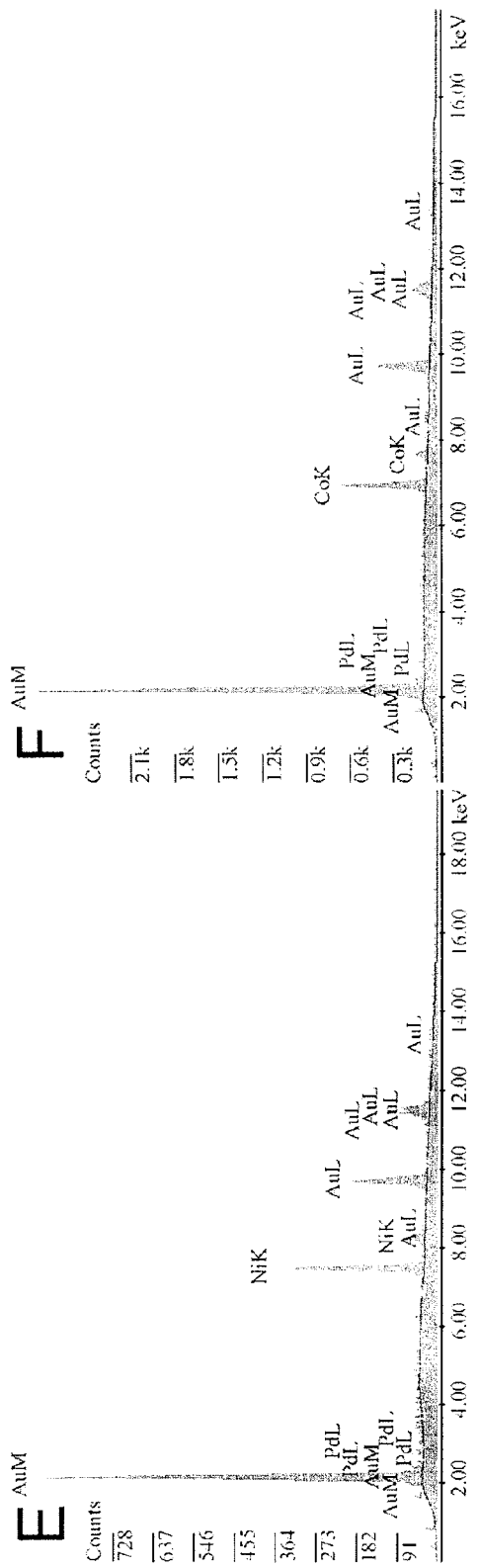
Figure 2 Contd.

```
                        SEQUENCE LISTING

<160> NUMBER OF SEQ ID NOS: 2

<210> SEQ ID NO 1
<211> LENGTH: 159
<212> TYPE: PRT
<213> ORGANISM: Tobacco mosaic virus

<400> SEQUENCE: 1

Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Glu Val Trp Lys Pro Ser Pro Gln Val Thr Val Arg Phe Pro
    50                  55                  60

Asp Ser Asp Phe Lys Val Tyr Arg Tyr Asn Ala Val Leu Asp Pro Leu
65                  70                  75                  80

Val Thr Ala Leu Leu Gly Ala Phe Asp Thr Arg Asn Arg Ile Ile Glu
                85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
        115                 120                 125

Leu Ile Val Glu Leu Ile Arg Gly Thr Gly Ser Tyr Asn Arg Ser Ser
```

-continued

```
                130                 135                 140
Phe Glu Ser Ser Ser Gly Leu Val Trp Thr Ser Gly Pro Ala Thr
145                 150                 155

<210> SEQ ID NO 2
<211> LENGTH: 480
<212> TYPE: DNA
<213> ORGANISM: Tobacco mosaic virus

<400> SEQUENCE: 2
atgtcttaca gtatctctac tccatttcag ttcgtgttct tgtcatcagc gtgggccgac      60
ccaatagagt taattaattt atgtactaat gccttaggaa atcagtttca accacaacaa     120
gctcgaactg tcgttcaaag acaattcagt gaggtgtgga aaccttcacc gcaagtaact     180
gttaggttcc ctgacagtga ctttaaggtg tacaggtaca atgcggtatt agacccgcta     240
gtcacagcac tgttaggtgc attcgacact agaaacagaa taatagaagt tgaaaatcag     300
gcgaacccca cgactgccga gacgttagat gctactcgta gagtagacga cgcaacggtg     360
gccataagga gcgcgataaa taatttaata gtagaattga tcagaggaac cggatcttat     420
aatcggagct ctttcgagag ctcttctggt ttggtttgga cctctggtcc tgcaacttga     480
```

METAL COATED VIRUS-BASED NANOELECTRODES AND METHOD OF ASSEMBLING OF SAME

CROSS-REFERENCE TO RELATED APPLICATIONS

This application is filed under the provisions of 35 U.S.C. §371 and claims the priority of International Patent Application No. PCT/US07/089032 filed on Dec. 28, 2007, which in turn claims priority to U.S. Provisional Patent Application No. 60/877,403 filed on Dec. 28, 2006, the contents of which are hereby incorporated by reference herein for all purposes.

STATEMENT AS TO FEDERALLY SPONSORED RESEARCH

This invention was made with Government support under Grant No. DEFG02-02ER45975. The Government has certain rights in the invention.

BACKGROUND OF THE INVENTION

1. Technical Field

The present invention relates to nano-scaffolds, and more specifically, to genetically engineered nanoscale metal reactive surfaces that are useful in nano-devices, including sensors, solar cells, batteries, electrodes, transistors, semiconductor chips and capacitors.

2. Related Technology

High surface area nanostructured materials have uses in an array of applications including electrodes, catalyst supports, thermal barriers, sensor arrays and energy storage devices. Increased surface areas are generally achieved through the synthesis of particles with high surface to volume ratios or the manufacture of nanostructured materials from bulk substrates.[1,2] Methods used to create high surface area nanostructures, such as laser ionization or lithography, generally require complex and expensive technologies that can limit the application of these materials. To avoid such limitations, researchers are increasingly investigating alternative methods for the self-assembly of high surface area nanostructured[9] materials and devices. One approach is templating materials onto biologically derived substrates. Biological templates such as nucleic acids and viruses have evolved to self-assemble into hierarchically ordered structures with high surface to volume aspects, making them ideal for the synthesis of high surface area nanomaterials.

Previous studies have functionalized DNA[3], virus particles and protein tubules[5-8] using a variety of methods to produce field effect transistors[9], battery electrodes[10] and memory devices[11]. Recent work has shown that electrostatically induced alignments of uniform macromolecules such as viruses can be used to produce two-dimensional monolayers of biological templates[12]. However, the assembly and surface attachment of biologicals has primarily relied on the random association of bio-templates onto device surfaces. The use of biological components in nanostructured materials also requires the development of strategies to functionalize these components upon assembly.

One area of particular interest is the development of methods to obtain continuous and uniform coatings of reactive metals. Most deposition strategies rely on the reduction of metal directly onto the surface of the biological template.[13-18] This methodology typically produces discrete metal particles that decorate the surface of the bio-template, but often lack the uniformity needed to produce highly conductive surfaces. As such, the arbitrary nature of this process can limit the usefulness of bio-templates in device assembly and represents a significant obstacle in creating high surface area nanostructured materials.

Thus, there is a need to develop new methodologies for the oriented and uniform assembly of bio-templates that easily adhere to device surfaces and also provide uniformity of metal surfaces to produce highly conductive surfaces.

SUMMARY OF THE INVENTION

The present invention relates to nanoscale devices comprising a genetically engineered virus that provides for active sites to interact and adhere to a metal surface and also provide a template for deposition of conductive metal clusters.

Specifically, in one aspect the present invention relates to nanoscale electrodes, wherein the electrodes comprise a genetically engineered Tobacco mosaic virus TMV including genetically introduced amino acid residues that provide a template for deposition of conductive metal clusters.

In another aspect, the present invention provides for a method of preparing a Tobacco mosaic virus having a plurality of genetically introduced amino acid residues for selective binding to a gold surface and also providing a reactive template for deposition of metal clusters to provide a high surface electrode. Preferably, the metal clusters include nickel or cobalt.

In a still further aspect, the present invention provides for an electrode comprising a substrate having a gold surface deposited thereon and a multiplicity of modified Tobacco mosaic viruses (TMV) positioned on the gold surface, wherein the modified TMVs comprise genetically introduced amino acid residues that provide a deposition site for nickel containing metallic cluster, wherein the introduction of the additional amino acid residues provide an increased metallic surface relative to a TMV without the genetically introduced amino acid residues.

Preferably the genetically introduced amino acid residue is at least one cysteine introduced to each subunit making up the TMV. Notably, the genetically introduced amino acid residues provide for selective binding to a gold surface and also provide a reactive template for deposition of conductive metallic clusters for an increased conductive surface.

Another aspect of the present invention provides for a nanoscale electrode comprising:
 a) a substrate surface having at least one area of gold deposited thereon;
 b) a multiplicity of genetically engineered Tobacco mosaic viruses TMV connected to deposited gold, wherein each of the genetically engineered Tobacco mosaic viruses comprises a multiplicity of subunits, wherein at least one of the subunits comprises at least one additional thiol containing amino acid residue; and
 c) a metallic conductive coating deposited on and connected to the at least one additional thiol containing amino acid residue of the genetically engineered Tobacco mosaic virus to generate metallic coated TMV virus.

Preferably, the additional thiol containing amino acid residue is a cysteine and the metallic conductive coating is nickel or cobalt having a thickness of from about 15 to 40 nm. Notably, the substrate surface may include a patterned, unpatterned, semicontinuous or continuous metallic surface.

In yet another aspect, the present invention provides for metallic nanotubes comprising genetically modified Tobacco mosaic viruses TMV core comprising recombinantly introduced amino acid residues for selective binding of a metallic coating to such amino acid residues. Preferably, a plurality of the metallic nanotubes are fused to a surface.

Another aspect of the present invention provides a method of preparing a nanoscale device having electrical conductivity, the method comprising the steps of:
(1) providing a substrate surface;
(2) providing a genetically modified Tobacco mosaic virus TMV core comprising at least one recombinantly introduced thiol containing amino acid residue in at least one subunit of the Tobacco mosaic virus, wherein the thiol containing amino acid residue is positioned and/or exposed on the outer surface of the TMV core;
(3) connecting at least one area of the genetically modified Tobacco mosaic virus TMV core to the substrate surface;
(4) reacting the one or more thiol containing amino acid residue with an activation solution to form charged thiol containing amino acid residue; and
(5) reacting the charged thiol containing amino acid residue with a solution comprising a metallic plating solution for metal deposition on the thiol containing amino acid residue to provide a metallic conductive coating.

A still further aspect of the present invention provides compositions comprising nanostructures of the present invention adhering to a substrate that can be any geometric shape including spherical, triangular, planar, rectangular, etc and retained in a composition, wherein the nanostructures are substantially monodisperse in length, width, or length and width.

Other aspects and advantages of the invention will be more fully apparent from the ensuing disclosure and appended claims.

DETAILED DESCRIPTION OF THE INVENTION

The present invention is directed to the discovery that a variety of nanostructures comprising a virus cage can be made and mixed to produce materials with both a variety of new applications as well as "tunable" applications, e.g. the ability to alter material properties, e.g. different electrical and/or magnetic properties, by the incorporation of different amino acid residues into the virus cage. This allows the directed synthesis of materials whose electrical properties are tailored by the size and composition of the particles, and by their assembly into mono- and multi-component two-dimensional ordered arrays which allows for tunable and externally controllable inter-particle interactions that modify the macroscopic material properties for future application as superior devices.

The present invention further provides for genetically encoding materials that provide for distinct structural size and geometric control for self-assembling components. Chemical modifications to the surface of the biological templates[19,20] or genetic modifications that incorporate high affinity amino acids or substrate specific peptides[21,22] into the template can enhance biotemplate coatings to produce more uniform metal depositions. The present invention provides for the use of Tobacco mosaic virus (TMV) as a template for the deposition of metals.

Figure 1:
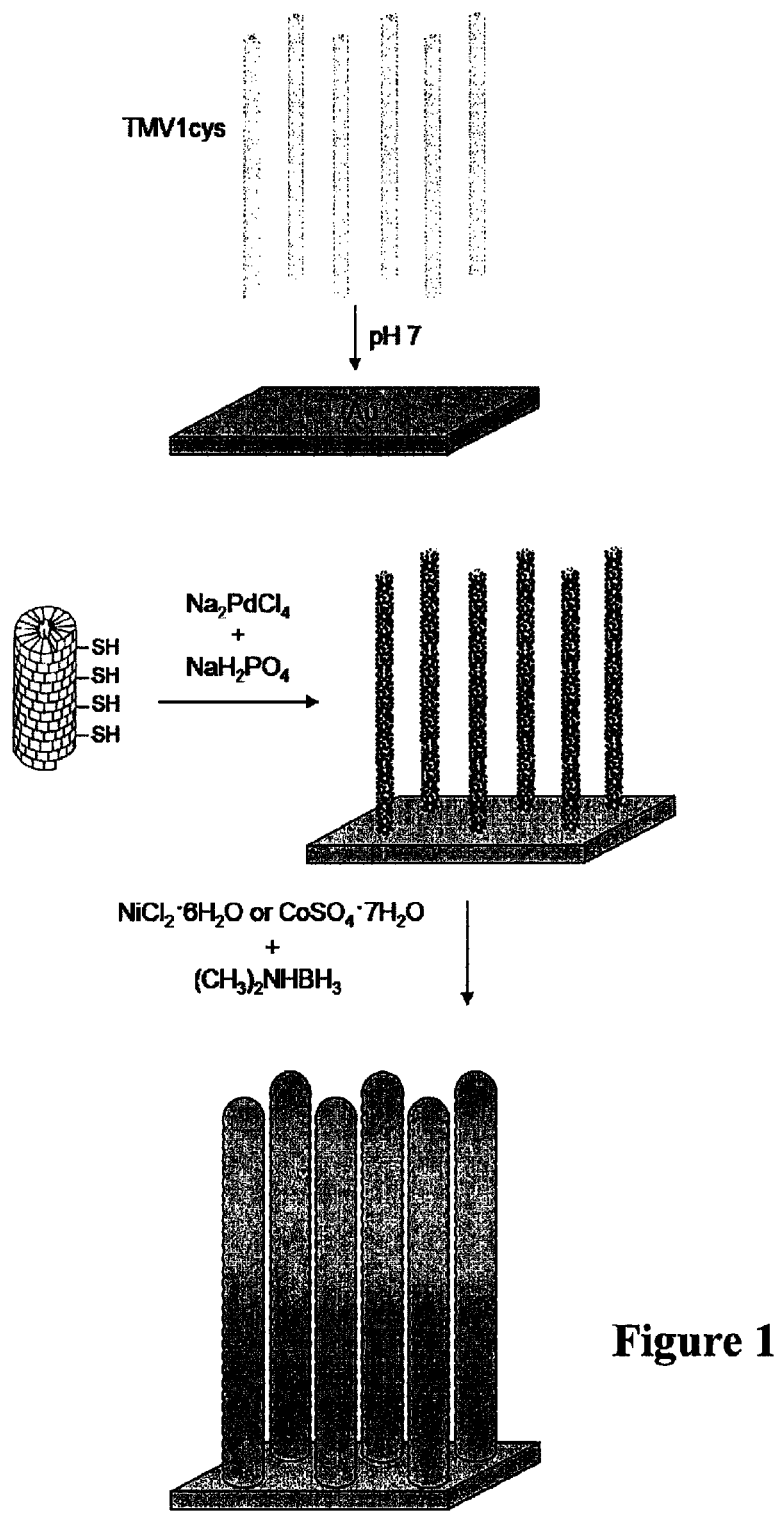
FIG. 1 shows the steps for the assembly of nickel or cobalt-coated TMV1cys templates and attachment to a gold surface.
Figure 2:
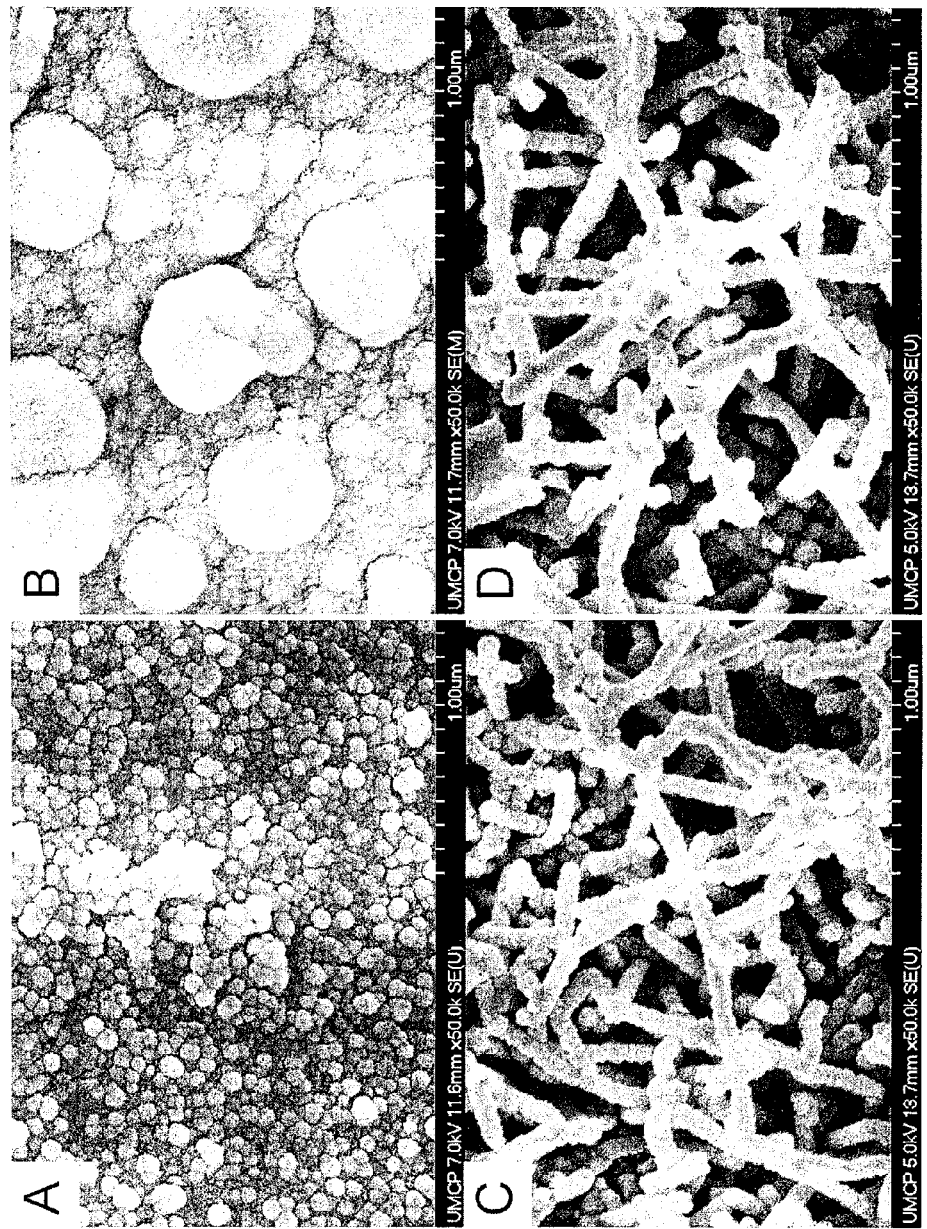
FIG. 2 shows FESEM images showing (a) a nickel-coated gold surface without TMV1cys, (b) a cobalt coated gold surface without TMV1cys, (c) a nickel-coated gold surface with 1 mg/mL TMV1cys, (d) a cobalt-coated gold surface with 1 mg/mL TMV1cys, and the corresponding EDX spectrum verifying the presence of (e) nickel and (f) cobalt respectively for the coated TMV1cys samples.
Figure 3:
FIG. 3 shows a TEM image showing a 70 nm thick cross section of nickel-coated TMV1cys attached perpendicular to a gold-coated mica surface. Coating thicknesses of nickel encasing each particle were measured at ~20 nm. Scale bar is equal to 300 nm.
Figure 4:
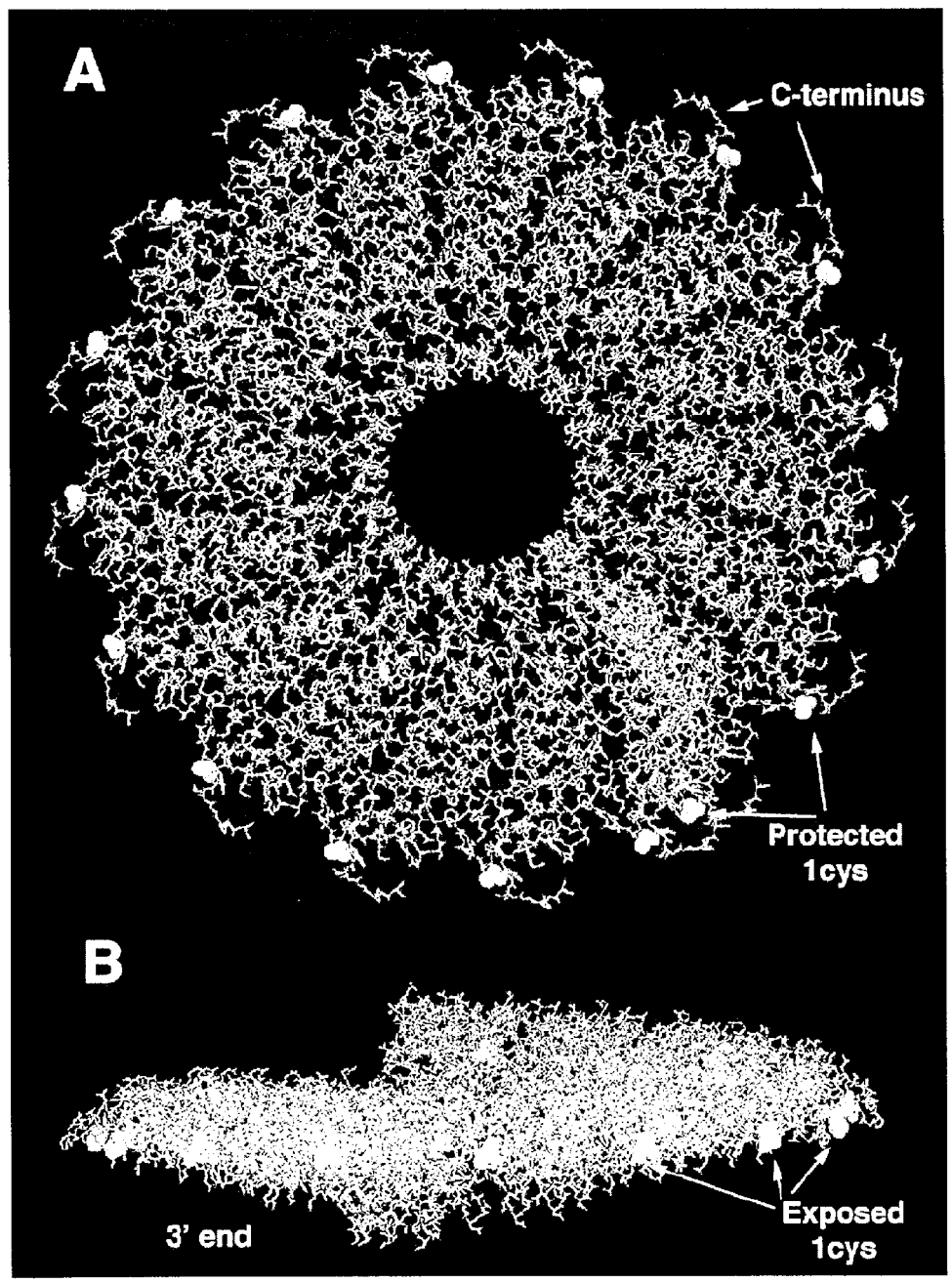
FIG. 4 shows a computer generated model diagramming the position of the 1cys mutations relative to the (a) outer rod surface and (b) the 3' end.

Generally, in the present invention, as illustrated in FIG. 1, TMV was genetically engineered to express a novel coat protein cysteine residue, TMV1cys, which was then used to vertically pattern TMV particles onto gold surfaces via gold-thiol interactions. Importantly, it was found that the TMV1cys readily bound to gold surfaces and remained attached during mineralization while the unmodified wild-type virus did not (data not shown). Then an electroless deposition strategy was used to show that surface assembled TMV1cys are mineralized in a uniform manner.

Notably, patterned TMV virion particles, with one or more added cysteine residues, function as robust templates for the reductive deposition of nickel and cobalt at room temperature via electroless deposition, producing dense carpets of oriented metal-coated viral templates. Mineralized surface assembled viruses significantly increased available surface area and enhanced electrode life and voltage output in a battery electrode system. The controlled self-assembly of these virus templates in an oriented manner combined with their enhanced functionalization to produce uniform high surface area electrodes represents a significant advance toward the manufacturing of biologically based devices.

TMV encodes a rod-shaped particle 300 nm in length and 18 nm in diameter with a 4 nm diameter hollow inner channel. Each TMV particle is comprised of ~2130 identical protein subunits (SEQ ID NO: 1) of molecular weight 17.5 kDa that self-assemble in a helix around a single strand of genomic virus RNA.[23] TMV particles are also stable in a wide range of temperatures (up to 60° C.) and pH values (~pH 2-10)[24], making the virus a durable biological template. Therefore, this virus can be to create tailor-made nanostructure electrode materials that exhibit improved structural stability and higher capacity.

In one embodiment, the subunits of TMV are genetically engineered to specifically bind to metal ions or metallic nanoparticles. Metallic coated nanotubes are synthesized using this engineered virus template. Specifically, to enhance mineralization, novel genetic modifications that introduce at least one thiol containing amino acid residue into each subunit of the virus and more preferably a cysteine is introduced near the amino terminus of each coat protein subunit which has been found to enhance significantly metal depositions. Within TMV, the amino terminus is located on the outer surface of the virion. Although the TMV coat protein contains a cysteine residue at position 27, it is embedded within the interior of the central helix bundle of the protein and is not accessible in the assembled virion.

Thus, in one embodiment, a TMV1cys template provides a highly selective template for the attachment of thiol reactive molecules. TMV1cys can be created by the insertion of a TGT codon in the third amino acid position within the coat protein open reading frame of the full-length TMV infectious clone (SEQ ID NO: 2 shows a representative open reading frame of unmodified U1 strain of TMV). Notably, the present invention also envisions the use of additional codons inserted into the TMV open reading frame, such as a TGT codon at positions 2 and 3 to create TMV2cys.

One of the advantages of the present invention is the ability to enable the introduction or synthesis and encapsulation of nanostructures including the TMV cage, which cannot be accomplished through techniques and means disclosed in prior art. Another substantial advantage over prior art is the ability to vary the distinct structural size of the viral cage, by adjusting the number of subunits making up the cage. The virus is approximately 300 nm but can be easily shortened or lengthened. Further, the density of the TMV cage structures and alignment of the structures can be predetermined by the amount of the cages adhering to a surface. Notably, if the packing is dense, the structure will resemble an essentially parallel packing alignment. As the density of structure is reduced, the alignment of the tubular structures will exhibit a random alignment that is more likely to be traverse to the surface.

Further, the present invention provides for modification of the surfaces and interfaces of the virus cage through chemical, physical and/or gene modification technology. These modifications can enable or prohibit attachment of other virus or protein cage structures, can provide a means to bind to targets of interest for medical applications, and can provide a means and method of fabricating two and three dimensional arrays of like, similar or different combinations of virus cages constrained on a surface or to other protein cage structures.

In the formation of useful arrays of the virus cages of the present invention, an essential element is a matrix of metallic material surrounding and adhering to each virus cage, which may be insulating, semiconducting, or conducting. It is an object of this invention to chemically, genetically or physically modify the outside of the virus cages to enable self-assembly of arrays through the utilization of other organic or inorganic materials.

Accordingly, the present invention provides compositions comprising a plurality of nanostructures. By "nanostructures" herein is meant a composition of a proteinaceous template, such as the TMV rod shape cage, that self-assembles to form a protein cage and loaded with a metallic material. In this context, "metallic material" includes both inorganic and organometallic materials, ranging from single atoms and/or molecules to large conglomerates of the same. By "loaded" or "loading" or grammatical equivalents herein is meant the introduction of non-native materials onto at least the exterior of the virus cage (sometimes referred to herein as "mineralization", depending on the material loaded).

The virus cages may be loaded with inorganic materials, including, but not limited to, metals, metal salts, metal oxides (including neat, doped and alloyed metal oxides), non-metal oxides, metal and non-metal chalcogens, sulfides, selinides, coordination compounds, organometallic species. Preferably, suitable metals include, but are not limited to, monovalent and polyvalent metals in any form depending on the end use of the nanostructure, including, but limited to aluminum, barium, cadmium, chromium, cobalt, copper, europium, gadolinium, lanthanum, magnesium, manganese, nickel, platinum, neodymium, titanium, yttrium, zirconium, terbium, lithium, zinc and iron, as well as other lanthanides. Metals that can possess magnetic properties may also be used.

Clusters of metallic material are readily deposited on the surface of the modified TMV template wherein the entire surface or a portion of the surface is covered with discrete clusters. The size of the distribution of the clusters can range from 2 and 15 nm in diameter with an average of from about 5 to 7 nm.

Notably, the nanostructures are preferably attached or connected to a substrate or solid support. By "substrate" or "solid support" or other grammatical equivalents herein is meant any material that can be modified to contain discrete sites or surfaces appropriate for the attachment of the nanostructures. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, mica, metals, inorganic glasses, plastics, etc. Generally the substrate is flat (planar), although as will be appreciated by those in the art, other configurations of substrates may be used as well; for example, three dimensional configurations can be used, for example by using previously micromachining or semiconductor manufacturing methods to create fine structures onto which the nanostructures are attached.

The nanostructures are generally distributed on the substrate for formation of protein arrays by modification of the protein cage to introduce reactive thiol (SH) groups on the exterior surfaces of the protein (done either genetically or chemically) and subsequent adsorbtion of the protein directly onto a Au or Ag surface. Other methods that may be used include the formation of activated self assembled monolayers on Ag, Au, Si, $SiO_2$ surfaces followed by adsorbtion of the proteins of the virus cage onto those surfaces. This will include making SAMs that are terminated with amines (cationic), sulfates, sulfonates, carboxylates, phosphonates etc (anionic), also activated headgroups such as succinimidyl esters, maleimides.

When the nanostructures are self assembled in an array format (e.g. on a solid support), the interstitial spaces between the virus cages can be modified to include additional materials, termed herein "spacer materials", including insulating, semiconductive and conductive materials, magnetically inert materials, etc.

Once made, the nanostructures of the present invention find use in a variety of applications. In general, methods, nanostructures, and arrays, according to the present invention provide a means to generate conducting materials having increased density of conductance and therefore an increased storage density. Further, the present invention provides nanostructures of an elongated and substantially spherical particles of about 40 nm to about 60 nm in diameter with little variation in size. That is, relative to methods taught in the prior art, methods according to the present invention provide nanostructures having a predictable diameter as provided herein.

This invention is further illustrated by the following examples which should not be construed as limiting.

Methods and Materials

TMV1cys and Virus Purification.

A coat protein mutant, TMV1cys, encoding an additional cysteine residue at the amino terminus of the virus coat protein was used for all experiments.[27] TMV1cys was created by the insertion of a TGT codon in the third amino acid position within the coat protein open reading frame of the full-length TMV infectious clone (SEQ ID NO: 2 shows a representative open reading frame of unmodified U1 strain of TMV). *Nicotiana tabacum*, cv *Xanthi*, a systemic TMV host, was inoculated with infectious RNA transcripts generated from the TMV1cys cDNA clone. Virus was harvested 20 days post inoculation and purified, as previously described[28]. The 1cys insertion in the coat protein open reading frame was verified by cDNA sequencing of reverse transcribed viral RNA.

As used herein, the term "protein" denotes a string of at least two amino acids linked together by peptide bonds. Proteins may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc. The modification may lead to a more reactive or stable protein but not of the modifications should substantially interfere with the desired activity of the protein.

Surface Assembly and Mineralization.

Concentrations of 0.01, 0.1, and 1 mg/mL TMV1cys in 0.1 M pH7 sodium phosphate buffer in the presence of the gold-coated silicon substrate were allowed to incubate overnight at room temperature. A two-step plating process[14, 15, 26] was employed to obtain continuous metal deposition on gold surface assembled TMV1cys. First, TMV1cys templates were activated with a palladium catalyst via the reduction of $Pd^{2+}$ to $Pd^0$ using a hypophosphite reducing agent. Concentrations of 0.6 mM $Na_2PdCl_4$ in 0.1 M $NaH_2PO_2.H_2O$ in the presence of the template were allowed to incubate overnight. Nickel and cobalt electroless plating solutions, at pH 7 and 9 respectively, were prepared from 0.1 M $NiCl_2.6H_2O$ or $CoSO_4.7H_2O$, 0.15 M $Na_2B_4O_7$, 0.25 M glycine, and distilled $H_2O$ with a 0.5 M $(CH_3)2NHBH_3$ reducing agent. Palladium catalyzed TMV1cys surfaces were submerged in the electroless plating solution for three to four minutes and were then rinsed with distilled water, dried and stored in air at room temperature. For cross-sectional viewing, a gold-coated mica surface was used, prepared from vacuum evaporated gold on freshly cleaved mica. Nickel coated Au-mica samples were embedded in Spurr's resin sectioned to 70 nm thickness with a diamond knife Sections were mounted on a carbon-coated formvar copper grid.

Coating Analysis.

Transmission electron microscopy (TEM) images of cross-sectioned nickel-coated TMV1cys attached to a gold-coated mica surface were obtained using a Zeiss EM 10CA transmission electron microscope operated at 80 kV. Field emission electron microscopy (FESEM) images of nickel and cobalt-coated TMV1cys attached to a gold coated silicon surface were obtained using a Hitachi S-4700 FESEM. Operational parameters ranged from 5-20 kV accelerating potential. Energy-dispersive X-ray spectroscopy (EDS) analysis for cobalt or nickel elemental presence was verified using an AMRAY 1820D SEM with an EDAX Genesis EDS system. X-ray photoelectron spectroscopy (XPS) analysis was carried out using a Kratos AXIS Ultra DLD Imaging XPS. High resolution scans were done for the Ni 2p3/2, O1s, N 1s, C 1s, and B 1s peaks. All data were acquired using monochromated Al k α X-rays and processed with CasaXPS software. For peak analysis, the nonlinear Shirley background subtraction was employed with curve fittings calculated using a Gaussian-Lorentzian product function. The carbon 1s peak was set to 248.8 eV[29,30] to account for any charging effects.

Battery Assembly and Testing.

Electrodes were held in 20 mL of KOH electrolyte with 1 cm spacing between the surfaces. Anodes consisted of 6 $cm^2$ zinc strips. Gold-coated silicon cut squares 0.5 cm×0.5 cm, ordered from SPI supplies (West Chester, Pa.), were used in NiO electrode fabrication. Virus-templated electrode performance was characterized by the repeated charging and discharging of the electrodes using a Solartron 1287A Potentiostat (Hampshire, UK). Electrodes were galvanostatically cycled at a constant rate of 2 $mA/cm^2$ and between 2.2 and 0.25 V with the discharge capacity calculated in the voltage range of 2.2 to 0.75 V.

Example 1

Analysis of Metallic Coating

Coating of FESEM analysis clearly showed that surface assembled TMV1cys templates were continuously coated with nickel and cobalt metals (FIG. 2). TMV1cys coating densities measured from FESEM micrographs indicated thicknesses of between 15 and 40 nm of deposited metal encasing each virus particle (FIG. 2). Coated surfaces remained stable even after vigorous rinsing to remove excess plating solution. EDS analysis confirmed the presence of nickel or cobalt for surface assembled TMV1cys templates (FIGS. 2*d* and *e*). Interestingly, surface assembled TMV1cys templates coated with metal primarily oriented vertically to the gold surface producing carpet like arrays of coated virus rods. Nickel-coated TMV1cys assembled onto gold-coated mica was thin sectioned for TEM analysis to confirm this orientation. Results showed the vertical attachment of the virus particles to the gold surface and confirmed nickel coating thicknesses of ~20 nm encasing each particle (FIG. 3). In addition, encased virus templates were shown to produce tubes with nickel metal uniformly covering the outer surfaces. One contributing factor in the ability of the virus templates to orient vertically on gold surfaces is the surface topography of TMV, which consists of alternating grooves and ridges that allow the virus to self-align.[23] The position of the 1cys mutation at the third codon position also likely contributes to the vertical positioning of the viral rods on the gold surface. Although surface exposed, the 1cys mutation is recessed within a groove and partially covered by the C-terminal arm of the coat protein (FIG. 4*a*). This position likely inhibits direct contact between the cysteine derived thiol and the gold surface, functioning to block virus binding along the outer circumference of the virus particle. However, because the two ends of a TMV particle display different coat protein surfaces, the position of the 1cys mutation would be sufficiently exposed to make direct contact with the gold surface at the end of the particle that contains the 3' genome sequence, termed the virus 3' end (FIG. 4*b*). Additionally, the length of surface assembled virus rods was on average 700±300 nm or about twice that of an individual TMV1cys particle. The end-to-end alignment of TMV1cys particles can occur readily in solution and would account for the greater than virion lengths observed upon surface assembly and metal coating.[17]

Example 2

Figure 5:
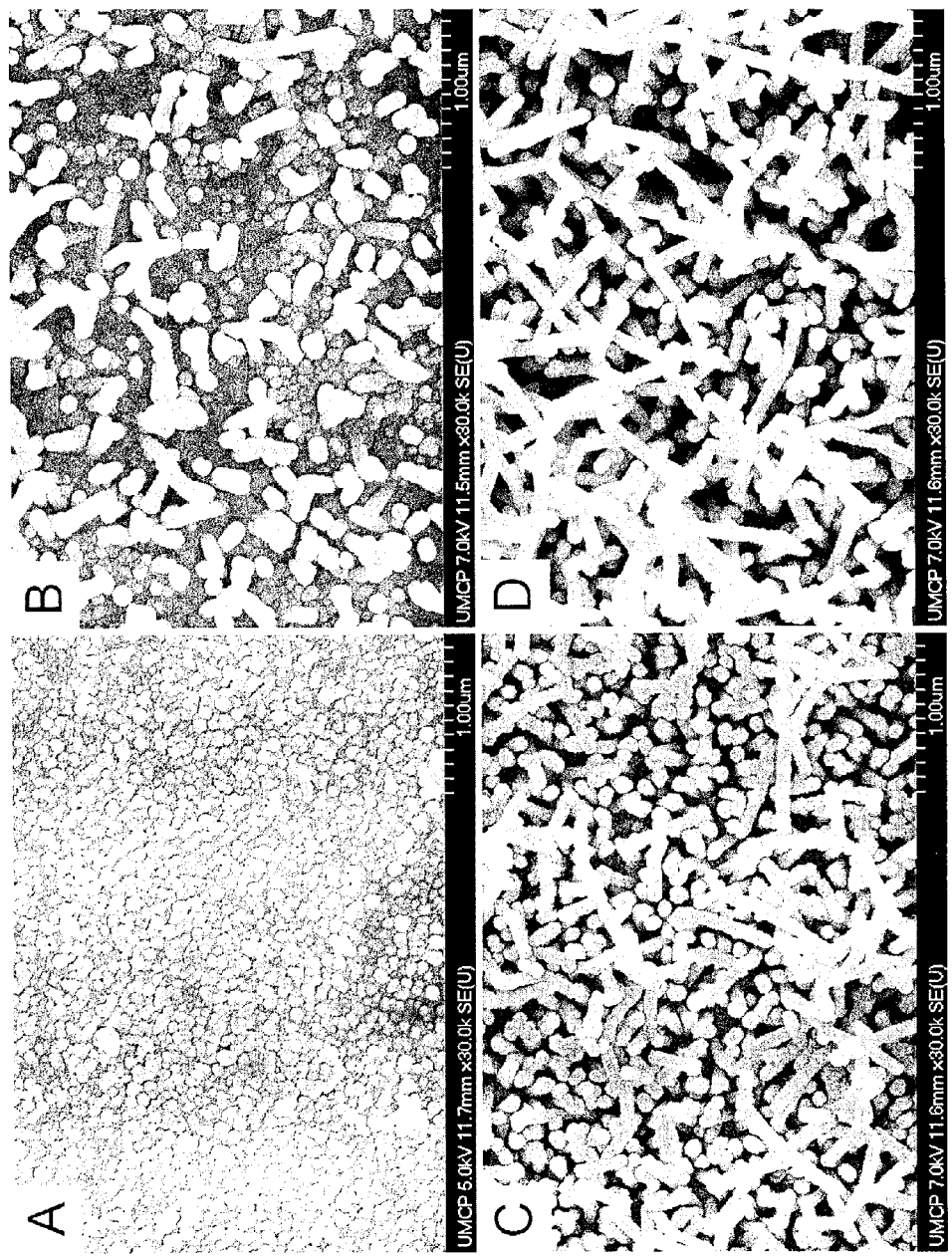
FIG. 5 shows FESEM images showing effects of concentration on the assembly of TMV1cys templates for nickel deposition. Concentrations of (a) 0 mg/mL TMV1cys, (b) 0.01 mg/mL TMV1cys, (c) 0.1 mg/mL, and (d) 1 mg/mL are shown.

Modulation of the surface assembly of TMV1cys was analyzed under a range of virus concentrations. FIG. 5 shows nickel-coated gold surfaces self-assembled using different concentrations of TMV1cys. Increases in the density of surface assembled TMV1cys particles were observed between a range of 0.01 and 0.1 mg/ml corresponding to particle count from about 30 to 70 per um$^2$. Based on FESEM analysis concentrations of 0.01 mg/mL resulted in TMV1cys particle counts of 31±4 per μm$^2$, while both 0.1 mg/mL and 1 mg/mL produced particle counts of 70±10 per μm$^2$. Using an average deposition thickness of 30 nm and particle length of 700 nm, the calculated increases in surface area are factors of 6±2 for assemblies done at a virus concentration of 0.01 mg/ml and 13±3 for those done at concentrations of 0.1 and 1 mg/ml. These findings demonstrate an ability to tune the surface assembly of TMV1cys and thus potentially control available surface area.

Figure 6:
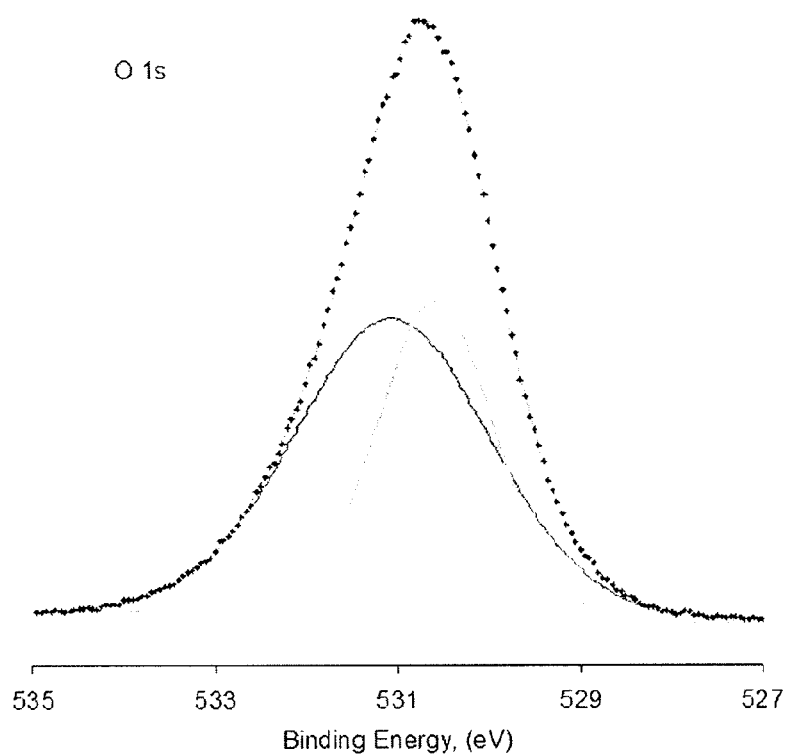
FIG. 6 shows the XPS spectrum of the Ni 2p3/2 peaks and O 1s peaks for nickel-coated TMV1cys attached to a gold-coated silicon wafer. An elemental analysis, using XPS, of nickel-coated TMV templates was performed to determine the suitability of this material to function as a battery electrode.
Figure 6:
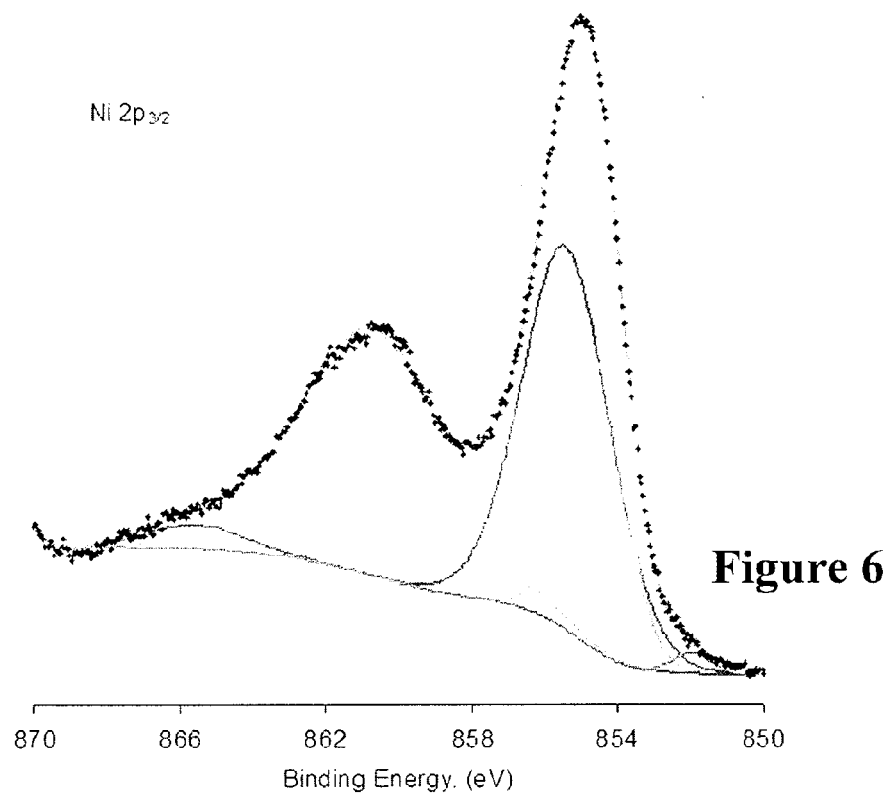

FIG. 6 shows high resolution Ni 2p3/2 and O 1s spectra from surface assembled nickel-coated templates. For NiO, a characteristic binding energy peak (BE) is reported at 854.6 eV with a satellite peak at ~861 eV.[31, 32] These BEs correspond to peaks of 854.8 and 860.9 eV measured from the virus-assembled surface, indicating that NiO represented the greatest constituent to the total nickel signal, comprising 18.7% from the main peak and 40.3% from the satellite peak. Additional peaks measured at 855.6, 865.5 and 852.2 eV corresponded to reported BE peaks[29, 30] of 855.6 and 865.5 eV for Ni(OH)$_2$ and of 852.2 eV for crystalline Ni. Thus, Ni(OH)$_2$ and Ni constitute 37.6% and 0.9% of the nickel signal obtained from assembled virus surfaces, respectively. Two peaks were assigned from the O 1s spectrum at 530.8 and 531.2 eV, representing contributions of 61.0% and 39.0% of the total oxygen signal. These values were consistent with those reported[30] for the oxygen in NiO and Ni(OH)2, respectively. This elemental analysis indicates that nickel coated virus surfaces contain levels of NiO sufficient for electrode function.

Example 3

Figure 7A:
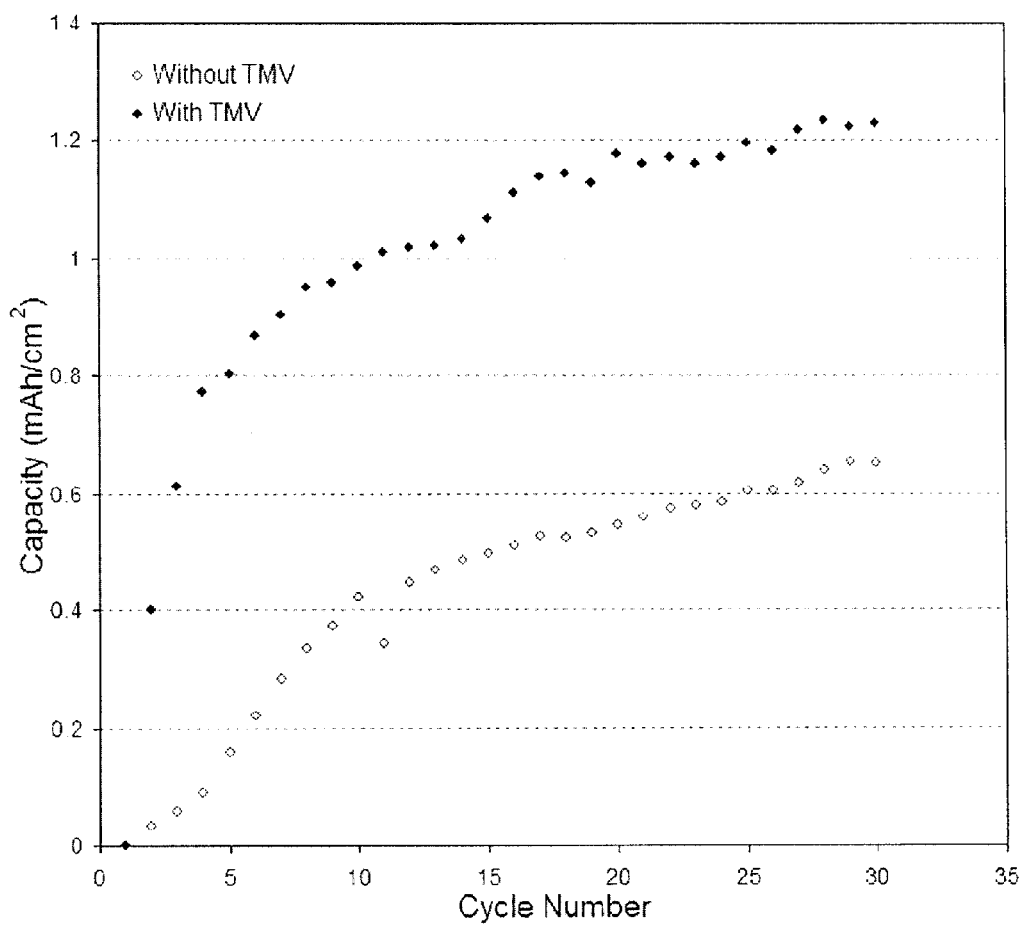
FIG. 7 illustrates (a) Diagram showing the discharge capacity vs. cycle number at 0.2 mA/cm constant current draw for the TMV1cys-templated electrode and the non TMV1cys-templated electrode. (b) Discharge curves for cycles 2, 15, and 30 at 0.2 mA/cm constant current draw for the TMV1cys-templated electrode and the non TMV1cys-templated electrode.

A NiO—Zn battery system was used to examine electrode activity of surface assembled virus-coated electrodes. Virus assembled and control electrodes were created using a 0.25 cm$^2$ gold-plated silicon wafer base. As the nickel plating process results in the deposition of nickel metal, electrodes were allowed to oxidize for 72 hours in air at room temperature prior to testing. Electrode capacity was shown to increase appreciably in the initial 15 cycles with smaller increases continuing to the end of the experiment at 30 cycles (FIG. 7a).

Previous work suggests the oxidation of electroless deposited nickel occurs to a depth of at least 6 nm, with an upper surface layer composed of Ni(OH)$_2$.[30] XPS results indicate a similar oxidation state for nickel-coated TMV. From these findings we expect two electrode chemistries will occur within this battery system as a result of oxidative processes.[33]

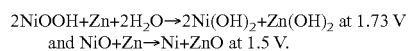

and NiO+Zn→Ni+ZnO at 1.5 V.

The small initial steady discharge observed (FIG. 7b) in the region of 1.7 V most likely belongs to the NiOOH reduction reaction, whereas the predominant discharge at the 1.5 V region most likely represents the NiO reduction reaction.

Figure 7B:
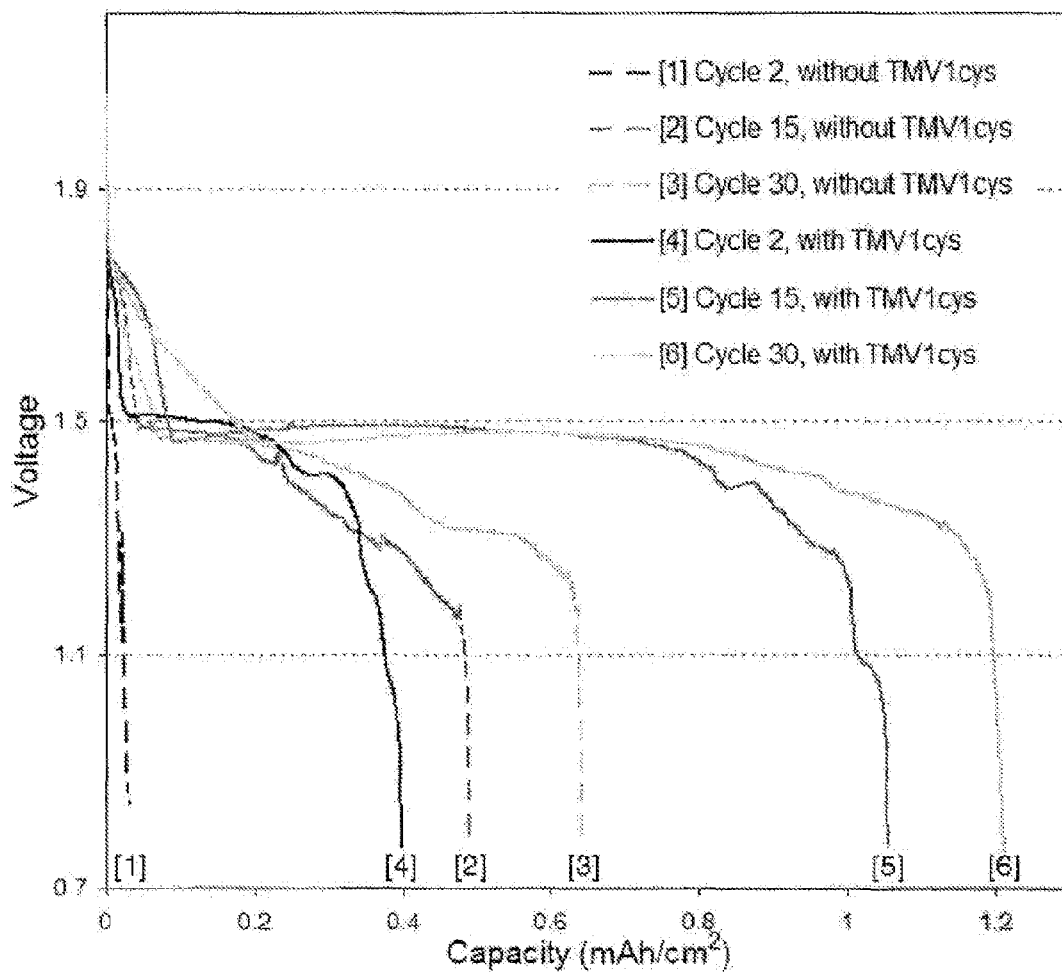

TMV1cys-assembled electrodes consistently out-performed non TMV1cys-templated electrodes, stabilizing after 15 cycles with a final two fold increase in capacity as shown in FIG. 7b. Although initial capacity increase showed an order of magnitude improvement for the TMV1cys-templated electrodes over non TMV1cys-templated electrodes, the swift decrease in capacity to a factor of 2 after 15 cycles may be due to the formation of a passivation layer on the zinc electrode decreasing the active anode surface area.[33] Ab initio calculations based on measurements from electron micrographs indicate ~10$^{-4}$ g/cm$^2$ electrode material is deposited onto the surface of assembled TMV1cys templates. This value was confirmed by microbalance measurements, indicating the presence of 10$^{-4}$ g/cm$^2$ of deposited nickel on the surface of virus-assembled electrodes. Weight contributions from the virus particles themselves were below the sensitivity limits of the balance and negligible to this calculation. Using these measurements, it was calculated that the specific discharge capacity was on the order of 10$^5$ mAh/g for the virus-templated electrode surface.

Figure 8:
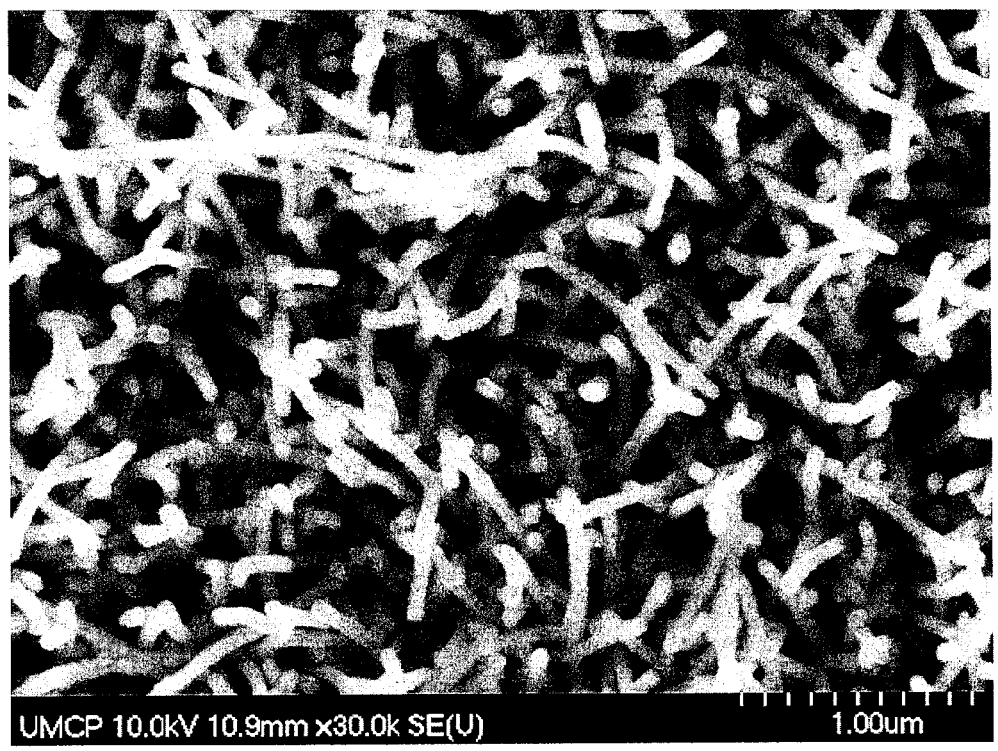
FIG. 8 shows a FESEM showing nickel-coated TMV-templated electrodes after 30 charge/discharge cycles.

In conclusion, the biologically derived components of the present invention are unique in that they can encode novel specificities as well as the ability to self-assemble into defined structures. Thus, they have tremendous potential for use in the development and application of a variety of nanoscale devices. One of the challenges in the use of biological components is the ability to integrate these components into devices in a functionally useful way. In the present invention, the integration of TMV1cys based nanotemplates onto a solid surface was accomplished to produce functional high surface area nanomaterials. This self-assembly process works at room temperature and under mild buffer conditions and produces nanostructured materials that are uniformly oriented and coated. The density of surface assembled virus and thus available surface area was easily tuned by varying the virus concentration of the assembly reaction. A simple electroless deposition method allowed the efficient and uniform metal coating of assembled virus. Once coated, surface attached viruses were highly stable under a variety of conditions including repeated washings with acetone and vacuum drying. This stability was apparent in electrode performance, with FESEM analysis showing no noticeable loss in the structure of the coated viruses after 30 charge-discharge cycles as shown in FIG. 8. Furthermore, based on observed particle densities this process is efficient with as little as 450 mg of virus required to coat a square meter of electrode surface. Although a simple gold-thiol interaction was used to assemble these virus templates, it should be noted that TMV can be assembled into more complex patterns. Thus, the combined ability to pattern these templates via several methods could potentially be used to assemble differentially functionalized viruses into complex nanoscale structures.

REFERENCES

The contents of all cited references are hereby incorporated by reference herein for all purposes.
(1) Wang, P. *Curr Opin Biotechnology* 2006, 17, 574-579.
(2) Yang, S. M.; Jang, S. G.; Choi, D. G.; Kim, S.; Yu, H. K. *Small* 2006, 2, (4), 458-475.
(3) Braun, E.; Eichen, Y.; Sivan, U.; Ben-Yoseph, G. *Nature* 1998, 391, (6669), 775-778.

(4) Flynn, C. E.; Lee, S. W.; Peelle, B. R.; Belcher, A. M. *Acta Materialia* 2003, 51, (19), 5867-5880.
(5) Mertig, M.; Kirsch, R.; Pompe, W. *Applied Physics A* 1998, 66, S723-S727.
(6) Behrens, S.; Wu, J.; Habicht, W.; Unger, E. *Chemistry of Materials* 2004, 16, (16), 3085-3090.
(7) Gao, X. Y.; Matsui, H. *Advanced Materials* 2005, 17, (17), 2037-2050.
(8) Matsui, H.; Pan, S.; Gologan, B.; Jonas, S. H. *Journal of Physical Chemistry B* 2000, 104, (41), 9576-9579.
(9) Keren, K.; Berman, R. S.; Buchstab, E.; Sivan, U.; Braun, E. *Science* 2003, 302, (5649), 1380-1382.
(10) Nam, K. T.; Kim, D. W.; Yoo, P. J.; Chiang, C. Y.; Meethong, N.; Hammond, P. T.; Chiang, Y. M.; Belcher, A. M. *Science* 2006, 312, (5775), 885-888.
(11) Tseng, R. J.; Tsai, C. L.; Ma, L. P.; Ouyang, J. Y. *Nature Nanotechnology* 2006, 1, (1), 72-77.
(12) Yoo, P. J.; Nam, K. T.; Qi, J.; Lee, S.-K.; Park, J.; Belcher, A. M.; Hammond, P. T. *Nat Mater* 7 2006, 5, (3), 234-240.
(13) Dujardin, E.; Peet, C.; Stubbs, G.; Culver, J. N.; Mann, S. *Nano Letters* 2003, 3, (3), 413-417.
(14) Knez, M.; Bittner, A. M.; Boes, F.; Wege, C.; Jeske, H.; Maiss, E.; Kern, K. *Nano Letters* 2003, 3, (8), 1079-1082.
(15) Knez, M.; Sumser, M.; Bittner, A. M.; Wege, C.; Jeske, H.; Kooi, S.; Burghard, M.; Kern, K. *Journal of Electroanalytical Chemistry* 2002, 522, (1), 70-74.
(16) Liu, W. L.; Alim, K.; Balandin, A. A.; Mathews, D. M.; Dodds, J. A. *Applied Physics Letters* 2005, 86, (25), 1-3.
(17) Shenton, W.; Douglas, T.; Young, M.; Stubbs, G.; Mann, S. *Advanced Materials* 1999, 11, (3), 253-256.
(18) Balci, S.; Bittner, A. M.; Hahn, K.; Scheu, C.; Knez, M.; Kadri, A.; Wege, C.; Jeske, H.; Kern, K. *Electrochimica Acta* 2006, 51, (28), 6251-6257.
(19) Royston, E.; Lee, S. Y.; Culver, J. N.; Harris, M. T. *J Colloid Interface Sci* 2006, 298, (2), 706-712.
(20) Schlick, T. L.; Ding, Z. B.; Kovacs, E. W.; Francis, M. B. *Journal of the American Chemical Society* 2005, 127, (11), 3718-3723.
(21) Lee, S. W.; Mao, C. B.; Flynn, C. E.; Belcher, A. M. *Science* 2002, 296, (5569), 892-895.
(22) Lee, S. Y.; Royston, E.; Culver, J. N.; Harris, M. T. *Nanotechnology* 2005, 16, (7), S435-S441.
(23) Namba, K.; Pattanayek, R.; Stubbs, G. *Journal of Molecular Biology* 1989, 208, (2), 307-325.
(24) Stubbs, G. *Seminars in Virology* 1990, 1, 405-412.
(25) Lee, S. Y.; Choi, J.; Royston, E.; Janes, D. B.; Culver, J. N.; Harris, M. T. *J Nanosci Nanotechnol* 2006, 6, (4), 974-81.
(26) Knez, M.; Sumser, M.; Bittner, A. M.; Wege, C.; Jeske, H.; Martin, T. P.; Kern, K. *Advanced Functional Materials* 2004, 14, (2), 116-124.
(27) Yi, H.; Nisar, S.; Lee, S. Y.; Powers, M. A.; Bentley, W. E.; Payne, G. F.; Ghodssi, R.; Rubloff, G. W.; Harris, M. T.; Culver, J. N. *Nano Lett* 2005, 5, (10), 1931-6.
(28) Gooding, G. V.; Hebert, T. T. *Phytopathology* 1967, 57, (11), 1285.
(29) Grosvenor, A. P.; Biesinger, M. C.; Smart, R. S.; McIntyre, N. S. *Surface Science* 2006, 600, (9), 1771-1779.
(30) Siconolfi, D. J.; Frankenthal, R. P. *Journal of the Electrochemical Society* 1989, 136, (9), 2475-2480.
(31) Carley, A. F.; Jackson, S. D.; O'Shea, J. N.; Roberts, M. W. *Surface Science* 1999, 440, (3), L868-L874.
(32) Hufner, S., Photoelectron Spectroscopy. Springer-Verlag: Berlin, 1995.
(33) Linden, D., Handbook of Batteries 2nd edition. McGraw-Hill Inc.: New York, 1995.
(34) Yi, H.; Rubloff, G. W.; Culver, J. N. *Langmuir* 2007, 23, (5), 2663-2667.

That which is claimed is:

1. A nanoscale electrode comprising:
   a) a substrate surface having at least one area of gold deposited thereon;
   b) a multiplicity of genetically engineered Tobacco mosaic viruses TMV connected to the deposited gold, wherein the multiplicity of metallic coated TMV viruses are aligned and perpendicular to the substrate surface, wherein each of the genetically engineered Tobacco mosaic viruses comprises a multiplicity of virus coat protein subunits, wherein each of the subunits consists of a single recombinantly introduced cysteine residue inserted between amino acid residue two and three of U1 strain of TMV to be positioned at residue three at the amino terminus of the virus coat protein subunit having an amino acid sequence of SEQ ID NO. 1, and wherein the single recombinantly introduced cysteine residue engineered at a specific location at the N-terminus coat protein structure directs the end attachment of rod shaped TMV1cys particles through thiol interaction onto gold coated surfaces; and
   c) a metallic conductive coating deposited on and connected to the single recombinantly introduced cysteine residue of the subunits of the genetically engineered TMV1cys core thereby providing the nanoscale electrode that is uniformly coated.

2. The nanoscale electrode according to claim 1, wherein the metallic conductive coating is nickel or cobalt.

3. The nanoscale electrode according to claim 2, wherein the nickel metallic conductive coating is approximately from about 15 to 40 nm.

4. The nanoscale electrode according to claim 1, wherein the metallic coated TMV has a density particle count positioned on the substrate of from about 30 per $um^2$ to about 70 per $um^2$.

5. The nanoscale electrode according to claim 1, wherein the nanoscale electrode exhibits a discharge capacity in the voltage range of 2.2 to 0.75 V.

6. The nanoscale electrode according to claim 1, wherein the substrate surface includes a patterned or continuous gold surface.

7. The nanoscale electrode according to claim 1, wherein the multiplicity of metallic coated TMV viruses are aligned and perpendicular to the substrate surface.

8. The nanoscale electrode according to claim 1, wherein the substrate surface is planar.

9. The nanoscale electrode according to claim 6, wherein the thiol amino acid residues provide for selective binding to the gold surface and also provide a reactive template for deposition of nickel or cobalt metallic clusters for a high surface electrode.

10. The nanoscale electrode according to claim 1, wherein the metallic coated TMV rods are substantially monodisperse in length, width, or length and width.

11. A method of preparing a nanoscale device having electrical conductivity, the method comprising the steps of:
   (1) providing a substrate surface having at least one area of gold deposited thereon;
   (2) providing a genetically modified Tobacco mosaic virus TMV core comprising a multiplicity of virus coat protein subunits, wherein each of the subunits consists of a single recombinantly introduced cysteine residue inserted between amino acid residue two and three of U1 strain of TMV to be positioned at residue three at the amino terminus of the virus coat protein subunit, having an amino acid sequence of SEQ ID NO. 1, and wherein the single recombinantly introduced cysteine residue is positioned for exposure on the outer surface of the TMV1cys to make surface contact only at one end of the rod shaped virus particle;
   (3) connecting the single recombinantly introduced cysteine residue at one end of the genetically modified Tobacco mosaic virus TMV1cys core to the area of gold deposited surface via a gold-thiol interaction;
   (4) reacting the cysteine residue with an activation solution to form charged cysteine; and
   (5) reacting the charged cysteine residue with a solution comprising a metallic plating solution for metal deposition on the cysteine residue to provide a metallic conductive coating and a uniform surface coating.

12. The method according to claim 11, wherein the metallic coating solution comprises nickel or cobalt.

13. The method according to claim 12, wherein the nickel metallic conductive coating is approximately from about 15 to 40 nm thick.

14. The method according to claim 11, wherein the substrate surface includes a patterned or continuous gold surface.

15. The method according to claim 11, wherein the substrate surface is planar.

16. The nanoscale electrode according to claim 1, wherein the electrode is a nanotube.

* * * * *